(12) United States Patent
Loser

(10) Patent No.: US 7,175,635 B2
(45) Date of Patent: Feb. 13, 2007

(54) MEDICAL DEVICE WITH A DRIVE UNIT FOR A NEEDLE

(75) Inventor: Michael Loser, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 501 days.

(21) Appl. No.: 10/240,396

(22) PCT Filed: Mar. 30, 2001

(86) PCT No.: PCT/DE01/01223

§ 371 (c)(1),
(2), (4) Date: Sep. 30, 2002

(87) PCT Pub. No.: WO01/74259

PCT Pub. Date: Oct. 11, 2001

(65) Prior Publication Data

US 2003/0109825 A1    Jun. 12, 2003

(30) Foreign Application Priority Data

Mar. 30, 2000  (DE)  ................ 100 15 510
Mar. 30, 2000  (DE)  ................ 100 15 513

(51) Int. Cl.
*A61B 19/00*  (2006.01)
(52) U.S. Cl. .................................................... 606/130
(58) Field of Classification Search ........ 606/130, 606/1

See application file for complete search history.

(56) References Cited

U.S. PATENT DOCUMENTS

| 3,835,854 | A | * | 9/1974 | Jewett ................... 604/159 |
| 4,383,532 | A | | 5/1983 | Dickhudt |
| 5,389,100 | A | * | 2/1995 | Bacich et al. ........... 606/108 |
| 5,397,323 | A | * | 3/1995 | Taylor et al. ........... 606/130 |
| 5,769,086 | A | | 6/1998 | Ritchart et al. |
| 5,882,294 | A | | 3/1999 | Storz et al. |
| 5,931,832 | A | * | 8/1999 | Jensen .................... 606/1 |
| 6,665,554 | B1 | * | 12/2003 | Charles et al. .......... 600/427 |
| 2004/0111004 | A1 | * | 6/2004 | Loffler et al. ........... 600/7 |

FOREIGN PATENT DOCUMENTS

| DE | 9416957 | 2/1995 |
| EP | 0595291 | 5/1994 |
| EP | 0682910 | 11/1995 |
| EP | 0678004 | 12/1995 |

* cited by examiner

*Primary Examiner*—(Jackie) Tan-Uyen T. Ho
(74) *Attorney, Agent, or Firm*—Harness, Dickey & Pierce, P.L.C.

(57) ABSTRACT

The invention relates to a medical device, with a guide for the mounting of a needle, in particular, a puncture needle and a drive unit for a needle in the guide canal. The guide is divided into two sections and, arranged between the sections, is a drive unit for the, preferably friction, drive of the needle.

25 Claims, 2 Drawing Sheets

MEDICAL DEVICE WITH A DRIVE UNIT FOR A NEEDLE

This application is the national phase under 35 U.S.C. § 371 of PCT International Application No. PCT/DE01/01223 which has an International filing date of Mar. 30, 2001, which designated the United States of America and which claims priority on German Patent Application numbers DE 100 15 513.8 filed Mar. 30, 2000 and DE 100 15 510.3 filed Mar. 30, 2000, the entire contents of which are hereby incorporated herein by reference.

FIELD OF THE INVENTION

The invention generally relates to a medical device with a guide for the mounting of a needle, in particular a puncture needle, and with a drive unit for a needle located in the guide.

BACKGROUND OF THE INVENTION

In medicine, needle punctures of anatomical structures, whether for diagnosis (biopsies) or for therapy (injections, drainage, etc.), represent a common and frequent intervention. Puncture needles are used which are inserted through the patient's skin and advanced until they reach a defined target (often a tumor or a metastasis). It is of particular importance in this respect that the needle is aligned precisely with the target before insertion. Various imaging techniques can be used to visually monitor the alignment procedure and the actual insertion of the needle. The most common imaging methods used for this purpose are ultrasound, fluoroscopy or computed tomography.

In fluoroscopy and computed tomography, X-rays are used to obtain the images. Handling surgical instruments or a puncture needle near to the X-ray field or even within the X-ray field exposes the physician to considerable radiation levels. Although lead aprons and other protective measures reduce the radiation dose, the radiation exposure of the physician's hands themselves is still significant.

Devices taking over the manipulation of the instruments in the X-ray field would be of help here. The physician would operate the devices manually or by remote control outside the X-ray field, depending on whether the device concerned is a passive or active (motorized) device.

In the case of tissue removal, the needles used are either biopsy punch needles (diameter 1 to 2.5 mm) for obtaining tissue samples for histological examination, or fine needles (diameter ca. 0.8 to 1.4 mm with a length of up to 20 mm) for aspiration biopsy for cytological tissue samples. Ever finer needles are used for injections.

The thinner and longer the needles however, the greater the danger of the needle buckling. When inserting the needle by hand, the physician has to take care to guide the needle steadily and without it buckling. For this purpose, fine needles are in most cases held tightly with one hand at the point of insertion and the other hand is used to apply the driving force at the end of the needle.

If the needle is to be inserted by remote devices, that is to say driven by a motor, then the danger of the needle buckling takes on particular importance.

From EP-A-0 682 910, EO-A-0 595 291 and U.S. Pat. No. 5,882,294, it is known in devices of the type, to divide the guide into two sections and to provide between both sections drive devices which cooperate with frictional engagement to drive the needle.

From U.S. Pat. No. 4,383,532 and DE 94 16 957 U it is also known, by use of an articulated arm, to provide for pivoting about a defined point of rotation in such a way that the articulated arm effects a pivoting movement of the needle about a first axis and a second axis, and in each case in a plane containing the point of rotation.

SUMMARY OF THE INVENTION

An object of an embodiment of the invention is to make available a device, in which the danger of the needle buckling is reduced. One aspect of an embodiment of the invention is the structural design of a needle drive for remote-operated insertion of the needle without risk of buckling of the needle.

According to an embodiment of the invention, an object may be achieved by a medical device with a guide for the mounting of a needle, in particular a puncture needle, and with a drive unit for a needle located in the guide. The guide is preferably divided into two sections. Preferably, the drive unit includes drive devices which are arranged between the sections and which cooperate with the needle in order to drive the latter. Further, the needle is preferably pivotable about a defined point of rotation, wherein one end of the guide corresponds to the point of rotation.

As a result of the drive device arranged between the two sections of the guide, the needle is guided optimally in that area in which driving of the needle takes place. This creates a homogeneous introduction of force and practically rules out the danger of the needle buckling. The drive devices preferably have at least one drive roller cooperating in frictional engagement with the needle, so that no changes need to be made to the needle to be able to drive it. Thus, commercially available needles can be used instead.

BRIEF DESCRIPTION OF THE DRAWINGS

An illustrative embodiment of the invention is shown in the attached diagrammatic drawings, in which.

DETAILED DESCRIPTION OF THE PREFERRED EMBODIMENTS

Figure 1:
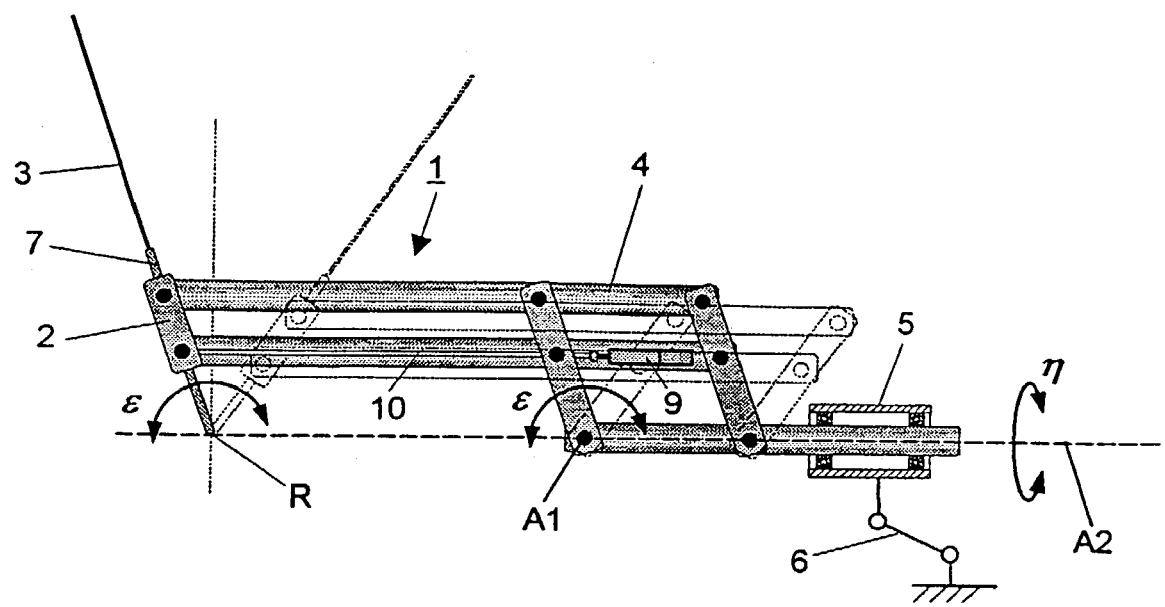
FIG. 1 shows a view of a medical device according to an embodiment of the invention.

In FIG. 1, a medical device according to an embodiment of the invention, labeled overall by reference number 1, is shown diagrammatically, with a needle guide system 2 for a needle 3, e.g. a puncture needle, which, as will be explained below, allows the needle 3 mounted in the needle guide system 2 to be pivoted three-dimensionally about a point of rotation R.

As will be seen from FIG. 1, the device 1 has an articulated arm 4 in the form of a parallelogram drive, at whose free end the needle guide system 2 is arranged. Because of the design of the articulated arm 4 as a parallelogram drive, a pivoting about the axis A1, which is at right angles to the plane of the parallelogram drive and therefore to the plane of the drawing in FIG. 1, through an angle $\epsilon$ likewise effects a pivoting through the angle $\epsilon$ about an axis extending parallel to the axis A1 through the point of rotation R defined by the geometry of the parallelogram drive.

The articulated arm 4 is additionally pivotable in a fixture 5 so as to pivot in direction η about an axis A2 extending through the point of rotation R.

Both axes A1 and A2 intersect and are perpendicular to one another. Since in addition the axis A2 extends through the point of rotation R, this represents as it were an invariable rotational point of the needle 3 whose position is defined solely by the geometry of the construction. By superpositioning of both pivoting movements about the axes A1 and A2, the needle 3 can be pivoted three-dimensionally about the point of rotation R which, in the medical application, is identical to the point of insertion. One of the possible settings of the needle 3 is indicated by broken lines in FIG. 1.

It will thus be apparent that, on the one hand, the needle 3 is pivotable by use of the articulated arm 4 about the defined point of rotation R, the articulated arm 4 effecting a pivoting of the needle 3 about a first axis in a plane containing the point of rotation R. Further, on the other hand, the articulated arm 4 is pivotable about a second axis A2 extending through the point of rotation R, in the sense of a pivoting of the plane containing the point of rotation R about the second axis of rotation.

The pivoting movements about the axes A1 and A2 are effected by motor devices, the corresponding motors not being shown in the figures for the sake of brevity.

The fixture 5 is in turn arranged displaceably on a holding arm 6 which for example is passive, i.e. not driven by motor, but instead manually adjustable.

The drive unit of the device according to an embodiment of the invention is described below with reference to FIGS. 1 and 2, which drive unit permits buckling-free, motor-driven insertion of a needle 3 into the body of a patient.

Figure 2:
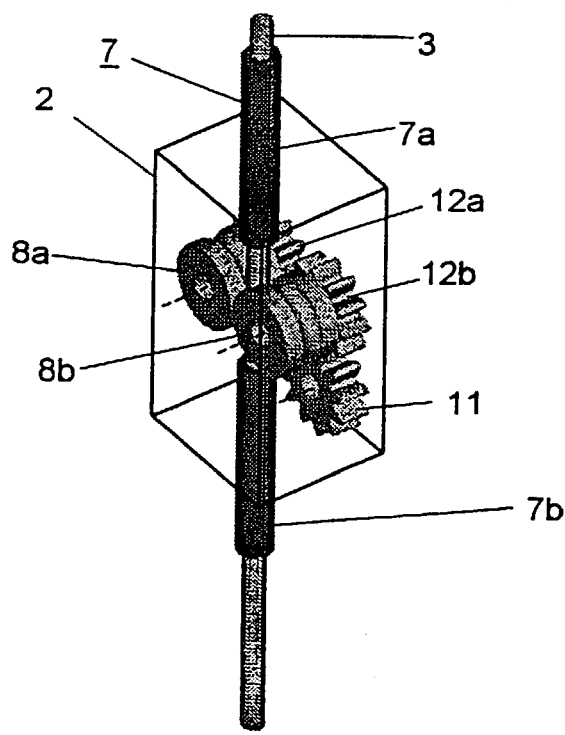
FIG. 2 shows a perspective view of a detail of the device according to FIG. 1.

As will be seen from FIG. 2, which shows diagrammatically the needle guide system 2 and, in combination with FIG. 1, the principle of the drive device of the needle 3, the core part of the needle guide system 2 is a special guide cannula 7 which is secured at the distal end, i.e. the free end, of the articulated arm 4 and, as has been explained, can be pivoted three-dimensionally within certain limits about the point of rotation R corresponding to the point of insertion.

The function of the guide cannula 7 is to receive the needle 3 securely and to guide it. The particular feature of the guide cannula 7 lies in the fact that it is divided into two sections 7a and 7b, with drive means for the needle 3 being located between the sections 7a and 7b.

As exemplary drive means, the drive unit has two rollers 8a, 8b which, as is illustrated, are preferably provided with a grooved profile and between which the needle 3 is guided. As soon as they are driven, the rollers 8a, 8b, designed in particular as rubber rollers, convert their rotary movement by friction, i.e. by frictional engagement, into a translational movement of the needle 3, so that the needle 3 can be inserted into a patient.

To apply the driving torque for the rollers 8a, 8b, the drive unit has a servomotor 9 which, according to FIG. 1 in the case of the illustrative example described, is located in the area of the lower horizontal element of the articulated arm 4. Via a drive shaft 10 and, if necessary, additional (gearing) components not shown in FIG. 2, the torsional moment is transmitted to the pair of rollers 8a, 8b via a toothed gear wheel 11. A uniform distribution of the torsional moment to both rollers 8a, 8b is ensured via two toothed wheels 12a, 12b which are connected directly to the rollers 8a, 8b.

The needle 3 is guided optimally in its drive area by means of the two sections 7a and 7b of the guide cannula 7 arranged tight on the rollers 8a, 8b, which guarantees a homogeneous and uniform introduction of force into the needle 3 and largely rules out the danger of the needle 3 buckling upon insertion.

Also in the area of the point of insertion of the needle 3 which, as has been mentioned, is identical to the point of rotation R, the danger of the needle 3 buckling upon insertion is largely precluded because the guide cannula 7 is arranged on the articulated arm 4 in such a way that its one end corresponds to the point of rotation R. By this arrangement of the guide cannula 7, it is in fact ruled out that the needle can buckle between drive and point of insertion.

This arrangement of the guide cannula 7 is also favorable because, in medical application, the device must first be positioned in such a way that the point of rotation R is located at the selected point of insertion, which is very easy because only the tip of the guide cannula 7 has to be placed at the point of insertion.

Figure 3:
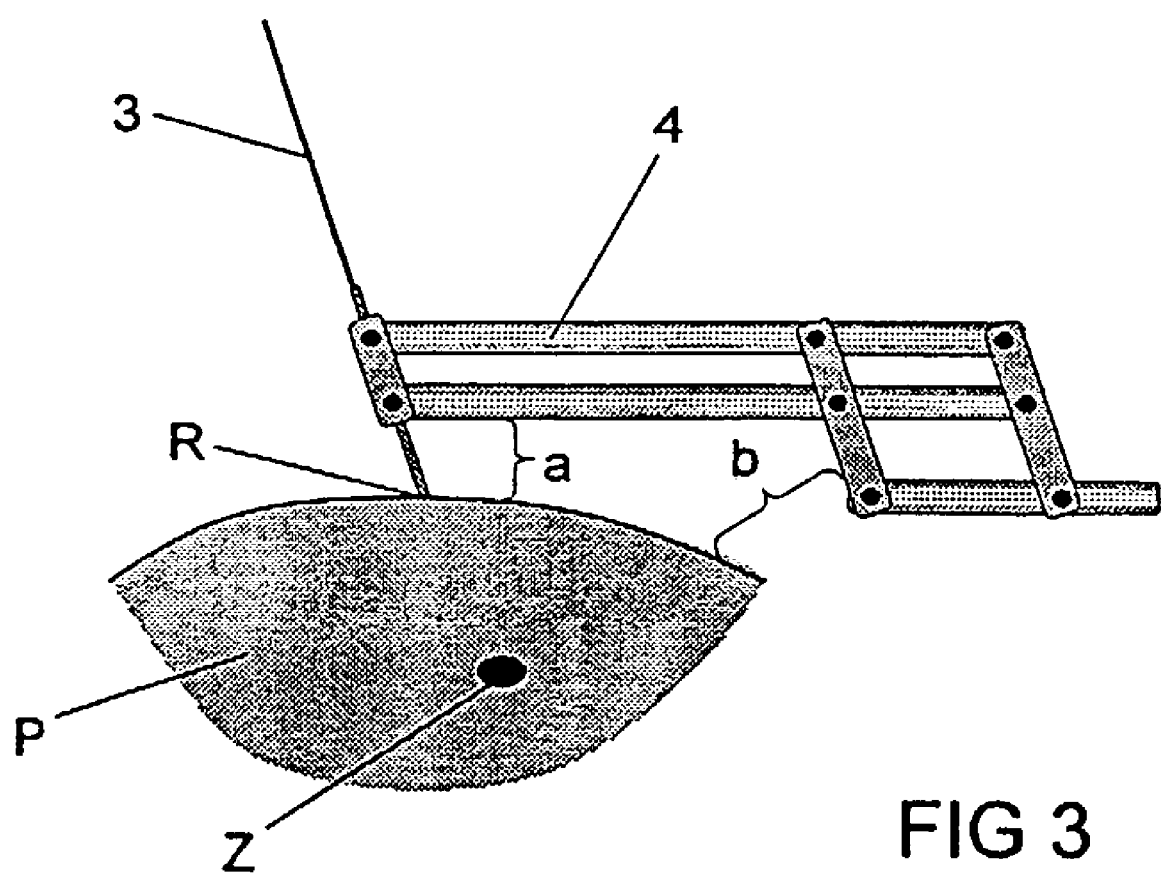
FIG. 3 shows a view of the device according to FIGS. 1 and 2 in use.

The described structural design ensures, on the one hand, sufficient space and freedom of movement, see the dimensions a and b indicated in FIG. 3, for versatile clinical application, the patient being indicated by P and the target, e.g. a tumor, being indicated by Z in FIG. 3. On the other hand, the described structural design guarantees that the puncturing is safe and free from buckling.

To be able to use needles of different diameters, the guide cannula 7 can easily be made exchangeable (in a manner not shown). When using rubber rollers, these generally have sufficient flexibility in order to be able to use needles of different diameter at least to a limited extent with the same pair of rollers.

As an alternative to the illustrative embodiment described, provision can be made for only one of the two rollers 8a, 8b to be driven.

The servomotor 9 and the drive shaft 10 can be arranged within one of the horizontal elements of the articulated arm 4 if the latter is of tubular design.

The drive unit according to the described illustrative embodiment is to be understood in its details as constituting only an example. The important thing is to use a guide which is divided into two sections, with drive means, particularly drive means with frictional engagement, being arranged between the sections for the needle.

This construction has the following advantages:

Buckling of the needle is largely ruled out both in the area of the needle drive and in the area of the insertion site.

If the device is used with fluoroscopy, all components in the X-ray field must be as radioparent as possible so as not to generate shadows in the image. By means of the design as a parallel drive, it is very easily possible to produce the front area of the guide system from radioparent plastics, while the motors and components of higher loading made of metal are located outside the X-ray field.

With the parallelogram drive, it is possible for no hinges to be present in the area of the point of rotation and there is therefore sufficient space and freedom of movement for versatile clinical application.

The whole construction can be made very compact, which in particular permits use in CT. Alternative systems, by contrast, often consist of arc-shaped structures, which in most cases are very bulky.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A medical device, comprising:
   a guide for mounting of a needle, the guide being divided into two sections; and
   a drive unit for the needle when mounted in the guide, the drive unit including drive means arranged between the two sections and cooperating with a mounted needle in order to drive the mounted needle, wherein the mounted needle is pivotable about a defined point of rotation and one end of the guide corresponds to the point of rotation, and wherein the guide is a guide cannula; and wherein the drive means includes a plurality of rollers, each roller being directly connected to one of a plurality of toothed wheels, and a toothed gear wheel for driving the plurality of rollers via the plurality of toothed wheels.

2. The medical device as claimed in claim 1, wherein the drive means includes at least one drive roller cooperating in frictional engagement with the needle when mounted.

3. The medical device as claimed in claim 2, wherein the at least one drive roller includes at least one rubber drive roller.

4. The medical device as claimed in claim 2, wherein the needle when mounted is pivotable by an articulated arm about a defined point of rotation, said articulated arm effecting a pivoting of the needle about a first axis in a plane containing the point of rotation.

5. The medical device as claimed in claim 4, wherein the articulated arm is in the form of a parallelogram drive.

6. The medical device as claimed in claim 4, wherein the articulated arm is pivotable about a second axis extending through the point of rotation, in the sense of a pivoting of the plane containing the point of rotation about the second axis of rotation.

7. The medical device as claimed in claim 6, wherein the articulated arm is in the form of a parallelogram drive.

8. The medical device as claimed in claim 1, wherein the needle when mounted is pivotable by an articulated arm about a defined point of rotation, said articulated arm effecting a pivoting of the needle about a first axis in a plane containing the point of rotation.

9. The medical device as claimed in claim 8, wherein the articulated arm is pivotable about a second axis extending through the point of rotation, in the sense of a pivoting of the plane containing the point of rotation about the second axis of rotation.

10. The medical device as claimed in claim 9, wherein the articulated arm is in the form of a parallelogram drive.

11. The medical device as claimed in claim 8, wherein the articulated arm is in the form of a parallelogram drive.

12. The medical device as claimed in claim 1, wherein the guide is for mounting of a puncture needle.

13. The medical device as claimed in claim 1, wherein the drive means is arranged tightly between the two sections.

14. The medical device as claimed in claim 1, wherein each section of the guide encloses the needle when mounted.

15. The medical device as claimed in claim 1, wherein the drive unit includes at least a pair of drive roller cooperating in frictional engagement with the needle when mounted.

16. The medical device as claimed in claim 15, wherein the at least a pair of drive roller includes at least a pair of rubber drive roller.

17. A medical device, comprising:
   a guide for mounting of a needle, the guide being divided into at least two sections; and
   a drive unit for driving the needle when mounted in the guide, the drive unit having a drive means being arranged between at least two of the sections and cooperating with a needle when mounted, wherein the needle when mounted is pivotable about a defined point of rotation and one end of the guide corresponds to the point of rotation, wherein the guide is a guide cannula, wherein the needle when mounted is pivotable by an articulated arm, and wherein said drive unit includes a servo motor located on the articulated arm and transmitting torsional movement via a drive shaft to the drive means.

18. The medical device as claimed in claim 17, wherein the drive unit includes at least a pair of drive roller cooperating in frictional engagement with the needle when mounted needle.

19. The medical device as claimed in claim 17, wherein the drive unit is arranged tightly between the two sections.

20. The medical device as claimed in claim 17, wherein each section of the guide encloses the needle when mounted.

21. The medical device as claimed in claim 17, wherein the drive unit includes at least one drive roller cooperating in frictional engagement with the needle when mounted.

22. The medical device as claimed in claim 21, wherein the at least one drive roller includes at least one rubber drive roller.

23. The medical device as claimed in claim 17, wherein the needle when mounted is pivotable by an articulated arm about a defined point of rotation, said articulated arm effecting a pivoting of the needle about a first axis in a plane containing the point of rotation.

24. The medical device as claimed in claim 23, wherein the articulated arm is pivotable about a second axis extending through the point of rotation, in the sense of a pivoting of the plane containing the point of rotation about the second axis of rotation.

25. The medical device as claimed in claim 23, wherein the articulated arm is in the form of a parallelogram drive.

* * * * *